United States Patent [19]

Gibbs et al.

[11] Patent Number: 5,716,347
[45] Date of Patent: Feb. 10, 1998

[54] GASTROSTOMY FEEDING PORTS WITH POSITIVELY SEALING ENTRANCE VALVES

[75] Inventors: Rebecca C. Gibbs, Winston-Salem; Mark DeLegge, Davidson, both of N.C.; Ronald D. Russo, Barrington, R.I.

[73] Assignee: Wilson-Cook Medical Inc., Winston-Salem, N.C.

[21] Appl. No.: 441,054

[22] Filed: May 15, 1995

Related U.S. Application Data

[63] Continuation-in-part of Ser. No. 202,443, Feb. 28, 1994.
[51] Int. Cl.$^6$ ...................................................... A61M 5/00
[52] U.S. Cl. ..................... 604/247; 604/27; 604/48; 604/256
[58] Field of Search ................... 604/247, 96, 27, 604/48, 277, 332, 256, 175

[56] References Cited

U.S. PATENT DOCUMENTS

| | | | |
|---|---|---|---|
| 5,336,203 | 8/1994 | Goldhardt et al. | 604/247 |
| 5,411,491 | 5/1995 | Goldhardt et al. | 604/247 |
| 5,413,565 | 5/1995 | Michels et al. | 604/247 |
| 5,501,426 | 3/1996 | Atkinson et al. | 604/256 X |

*Primary Examiner*—Michael Powell Buiz
*Assistant Examiner*—N. Kent Gring
*Attorney, Agent, or Firm*—Woodard, Emhardt, Naughton Moriarty & McNett

[57] ABSTRACT

Gastrostomy feeding ports are disclosed which remain positively sealed after repeated and extensive use. In one embodiment, a valve housing defines an inner passageway to provide fluid communication into a long term indwelling catheter and includes a rigid compression collar portion which defines a valve member receiving cavity within the inner passageway. The resilient valve member has an outer peripheral edge which generally conforms in shape to the valve member receiving cavity but is larger in dimension than the cavity when uncompressed. The resilient valve member also includes an outer wall portion which extends away from the outer peripheral edge of the diaphragm portion and which generally conforms in shape to the cavity. The resilient valve member is compressively fitted within the receiving cavity by the advancing of the outer wall portion into said cavity to thereby cause the outer peripheral edge to be compressed in dimension to fit within the cavity, with the compression collar pressing inwardly against the outer peripheral edge of the diaphragm portion to apply laterally compressive forces which bias the slit toward a normally closed position. Additional embodiments are disclosed which provide for the direct conversion of an implanted PEG tube into a low profile feeding port, and which further provide for the direct secure connection to an enteral feeding tube adapter.

29 Claims, 7 Drawing Sheets

GASTROSTOMY FEEDING PORTS WITH POSITIVELY SEALING ENTRANCE VALVES

This is a continuation-in-part of copending application Ser. No. 08/202,443 filed on Feb. 28, 1994 entitled Gastrostomy Feeding Port with a Positively Sealing Entrance valve.

BACKGROUND OF THE INVENTION

This invention relates to medical devices, and particularly relates to gastrostomy feeding ports which use check valves to prevent reflux of gastric contents out the entrance opening of the device during use.

Gastrostomy feeding ports provide access to the stomach at a stoma site. Such ports are typically left in place over a prolonged period of time and are used for feeding and medicating the patient over this period. Some of these devices include check valves which serve to prevent the reflux of gastric contents through the port because the leakage of gastric contents, which is highly acidic, can cause severe skin burns or tissue maceration leading to chronic skin infections. Valves that have been used in prior art gastrostomy feeding ports, however, do not always work as intended to prevent reflux, particularly after many repeated uses. Consequently, gastrostomy feeding ports are often supplied with closure caps which positively seal the port entrance while the port is not being used.

Gastrostomy feeding ports are usually short in length, low profile, and fit fairly flush to the skin surface. U.S. Pat. No. 4,944,732 describes one such device, which is commercially available as the Gastro-Port from Sandoz Nutrition Corp. The Gastro-Port includes an anti-reflux valve which is located outside the body in a removable screw cap. Since the valve portion is removable it can be repaired or replaced if needed without needing to replace the entire feeding port. The Button Replacement Gastrostomy Device is another commercially available gastrostomy feeding port which includes an anti-reflux valve. In the Button device, the anti-reflux valve is located in the distal tip of the device inside the stomach. Both the Button and Gastro-Port devices have closure caps to seal off or plug up the entrance opening in case the valves clog up or leak.

Other valve structures for catheter ports are shown in the prior art in the Bodai U.S. Pat. No. 4,351,328 and the hemostasis valve of Guest U.S. Pat. No. 5,000,745 and the valve of Suzuki U.S. Pat. No. 4,673,393. The Bodai valve incorporates a series of membranes which seal under the influence of the material's own resiliency. Both the Guest and Suzuki valves also provide a sealing effect owing to the resiliency of multiple stacked membrane valves with oriented slit openings to prevent leakage. These membrane structures tend to become stretched by repeated use, causing the valves to lose their ability to positively seal closed and leakage will begin to occur. Since the devices of Bodai, Guest or Suzuki are short term use devices, however, their valve structures need to function properly for only a few procedures before being removed or replaced. These valve structures are, therefore, adequate for their intended purposes, although they would not prove to be reliable over long term and repeated use.

Some devices in the general medical art have included valve structures which apply compressive force in some form against the valve opening to bias the valve towards a closed position. See, for instance, U.S. Pat. Nos. 3,853,127 to Spademan; 4,430,081 to Timmermans; 5,114,408 to Fleishhaker et al.; 5,125,903 to McLaughlin et al.; and 5,261,885 to Lui. While such devices may be satisfactory for their intended purposes, they generally do not provide a biased-diaphragm valve structure that is both easy to construct and assemble and will operate reliably through long term, repeated insertion and removal of an enteral feeding tube adapter.

A long term indwelling catheter or feeding tube, on the other hand, such as a gastrostomy feeding port, needs to provide a positive seal for many repeated uses over a long period of time. Since the valves of the prior art have not provided such a reliable seal, closure caps, as discussed above, have been used to ensure that leakage does not occur. Closure caps, however, are inconvenient because they need to be removed prior to each use of the port and reapplied onto the port after each such use. Over the course of time that a single port is left in place, this would involve hundreds of times that the cap would have to be removed from and replaced back onto the port. And should the cap be forgotten or not properly closed about the port even a single time, unintended leakage may consequently occur.

Wherefore, there is a need for a new long term indwelling catheter, particularly a gastrostomy feeding port, with an entrance valve that provides a positive sealing effect over the course of many recurrent uses of the valve and over the extended period of time that the port is left in place on a patient. Such a device would eliminate the need for a closure cap and would be both safer and more convenient to use than devices that have been provided in the past.

Prior to the implantation of a low profile gastrostomy port, it is common to implant a long, smooth walled Percutaneous Endoscopic Gastrostomy (PEG) tube for enteral feeding or medication. After a time, the PEG tube is removed and replaced with a low profile device, which is more convenient to the patient, especially when a bedstricken patient becomes able to resume a more mobile lifestyle. It is common to remove the PEG tube in its entirety and replace the PEG with a low profile device in the stoma site where the PEG tube had been. While it would be disirable to reduce the trauma and increased risk of infection resulting from completely removing the PEG tube by, instead, directly converting the PEG tube that has already been placed into a low profile device, the converting port device must securely and reliably attach to the PEG tube so that the connection does not loosen over the length of time that the port is left in place. Accordingly, there is a need for a device which directly converts a long PEG feeding tube into a reliable low profile gastostomy feeding port. The conversion should be easy to accomplish and provide for the reliably secure connection of the valve mechanism to the implanted PEG tube.

There is a further need to provide a gastrostomy port device which provides for the securely sealed direct connection to a standard enteral feeding adapter. Such a port would be more convenient as it would remove the need to use intermediate tubing connections.

SUMMARY OF THE INVENTION

The present invention provides a long term indwelling catheter with an improved one-way entrance seal module which will remain positively sealed closed after repeated and extensive use. The invention is especially useful when used as part of a low profile enteral gastrostomy feeding port where the valve and port might be left indwelling in a patient for up to a year and where a positive seal needs to be maintained even after hundreds of repeated uses.

A device according to the present invention incorporates a seal module which includes a valve housing and a resilient valve member contained therein. The valve housing defines an inner passageway to provide fluid communication into a long term indwelling catheter and includes a rigid compression collar portion which defines a valve member receiving cavity within the inner passageway. The resilient valve member has a diaphragm portion which has an "S" shaped slit therein and an outer peripheral edge which generally conforms in shape to the valve member receiving cavity but is larger in dimension than the cavity when uncompressed. The resilient valve member also includes an outer wall portion which extends away from the outer peripheral edge of the diaphragm portion and which generally conforms in shape to the cavity. The resilient valve member is compressively fitted within the receiving cavity by the advancing of the outer wall portion into said cavity to thereby cause the outer peripheral edge to be compressed in dimension to fit within the cavity, with the compression collar pressing inwardly against the outer peripheral edge of the diaphragm portion to apply laterally compressive forces which bias the slit toward a normally closed position.

The resilient valve member is made of a one-piece resiliently molded valve with a flat membrane. The "S" shaped slit therein is formed by two arcically shaped leaves. The valve member is cylindrically shaped and is compressively fitted into the likewise cylindrically shaped compression collar to bias the arcical leaves to a positively sealed closed position. Feeding adapters can be repeatedly inserted through the valve and connected directly with the catheter lumen to deliver unobstructed enteral formula directly into the patient. Removal of the adapter returns the valve immediately to its positively sealed position due to the compressive forces of the collar about the arcically shaped leaves.

The valve remains compressively biased towards its sealed closed position when not in use, and is not permitted to stretch or deform which can lead to leakage. The one-way entrance seal permits convenient insertion of an obturator to help in insertion of the catheter into the body and the seal also permits convenient insertion of a feeding adapter which can be used for either feeding or decompression of the stomach. It needs no separate closure plug, or removal of a screw cap, or different feeding adapters, or complicated decompression tubes. This valve structure allows the device to be lower in profile and closer to the skin surface, and helps to make the device more convenient, less complicated, and easier to use than other devices in the prior art. The device is especially useful for active children who require low profile feeding ports.

Additional embodiments are disclosed which provide for the direct convertion of an implanted PEG tube to a low profile long term feeding device, and which further provide for the direct secure connection to an enteral feeding adapter without the need for an extension tube as an intermediate connector.

Accordingly, it is a primary object of the present invention to provide an improved one-way entrance seal module for a medical catheter.

Another object of the present invention is to provide an improved gastrostomy feeding port utilizing a one-way entrance seal.

Another object of the present invention is to provide an improved gastrostomy feeding device with an externally located entrance seal.

Another object of the invention is to provide an improved gastrostomy feeding device utilizing a one-way seal that usefully converts an implanted PEG tube into a low profile feeding device.

Another object of the invention is to provide a low profile gastrostomy feeding port which incorporates a one-way seal and which provides for the securely sealed direct connection to an enteral feeding adapter.

Another object of the present invention is to provide a gastrostomy feeding port which is less complicated, easier to use, and less expensive than other commercially available products.

Other objects, features, and advantages of the invention shall become apparent from the detailed drawings and descriptions which follow.

DESCRIPTION OF THE PREFERRED EMBODIMENT

Figure 1:
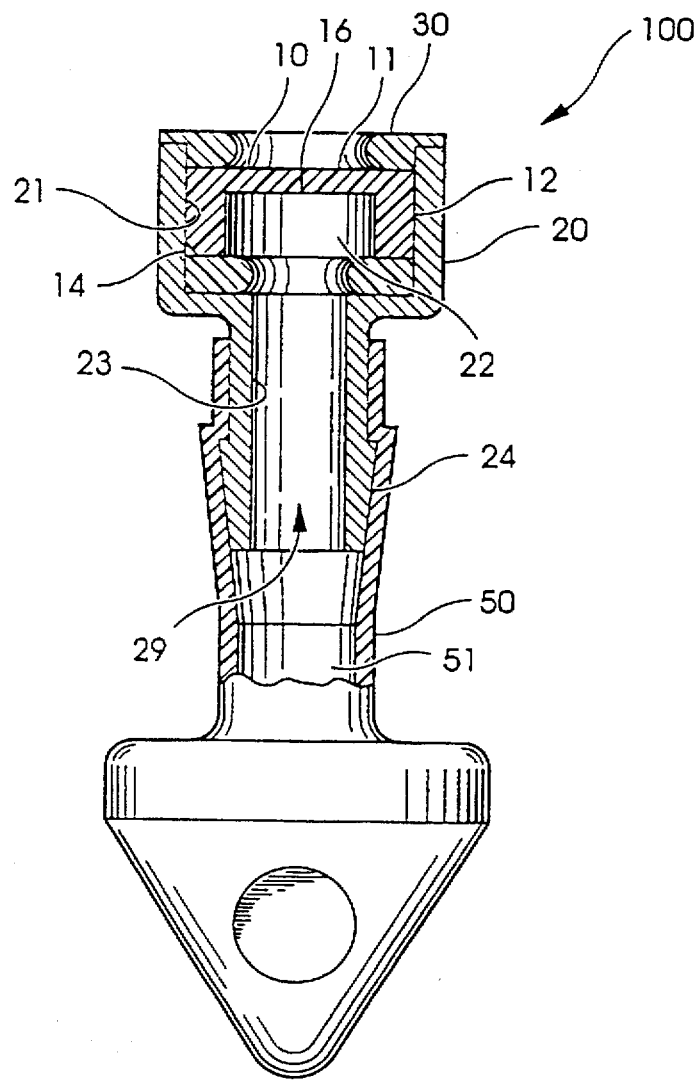
FIG. 1 is a side, partially cross-sectioned view of a gastrostomy port of the present invention incorporating a positively sealing one-way entrance valve.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
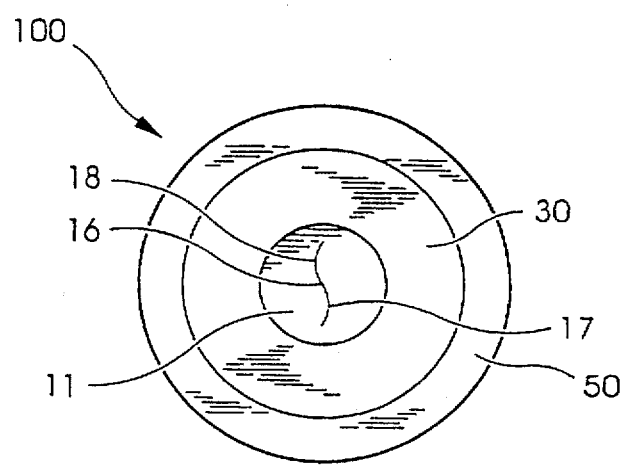
FIG. 2 is a top plan view of the gastrostomy feeding port of FIG. 1.

Referring now to FIGS. 1 and 2, there is shown a gastrostomy feeding port 100 which includes resilient valve member 10, valve housing 20, retainer cap 30, o-ring seal 40, and tubular/tip member 50. Resilient valve member 10 is made of silicone rubber, and has been constructed as a molded one-piece component and is preferably made from shore A 50 to 60 durometer high tear strength medical grade silicone. Diaphragm portion 11 of valve 10 is about 0.050 inches thick and about 0.325 inches in diameter and has a centrally located S-shaped slit 16 therein. Valve member 10 further has an outer cylindrical wall portion 12 which extends downwardly from the peripheral edge of diaphragm portion 11. O-ring 40 is preferably made of medical grade silicone as well, in the range of shore A 60 to 65 hardness.

Valve housing 20 defines an inner passageway 29 therethrough and includes rigid compression collar portion 21 which defines receiving cavity 22, annular seating portion 23 for seating of an adapter, and annular barb 24 for securing attachment to tubular/tip member 50. Valve housing 20 is injection molded from a rigid plastic such as lexan or polypropylene, but could be a machined part of stainless steel, or made of other suitable biocompatible material as well. Retainer cap 30 is preferably made of the same material as valve housing 20.

To assemble the valve structure for gastrostomy port 100, o-ring seal 40 is first placed into cavity 22 defined by compressive collar portion 21 of valve housing 20. Valve member 10 is then "press" fit into valve housing 20 by first fitting outer cylindrical wall portion 12 of valve member 10 into compression collar 21 and then applying even pressure to advance valve member 10 into cavity 22. The lower portion of cylindrical wall portion 12 of valve member 10 has a chamfered edge 14 to facilitate the introduction of valve member 10 into cavity 22. Also, isopropyl alcohol, which readily evaporates, can be used as a lubricant to aid in the press fitting of valve member 10 into valve housing 20.

As valve member 10 is advanced into cavity 22, cylindrical wall portion 12 is compressed to conform to the size of cavity 22. The compression of cylindrical wall portion 12, in turn, applies an evenly distributed compressive force on diaphragm portion 11 to cause diaphragm portion 11 to be evenly compressed and to thereby fit within cavity 22 without buckling or distorting. Once valve member 10 has been fully seated into valve housing 20, compression collar 21 acts with an inwardly directing compressive force to actively bias leaves 17 and 18 of "S" slit 16 on diaphragm portion 11 to positively seal valve member 10.

After valve member 10 has been seated into cavity 22, retainer cap 30 is placed on the top portion of valve housing 20 and affixed thereto. Attachment may be made by use of a suitable biocompatible solvent cement, or by ultrasonic welding. Once in place, retainer cap 30 does not exert any axial compressive force upon valve member 10, which could cause distortion of the sealing arrangement, and preferably only rests on the surface of diaphragm portion 11 or allows for a small gap therebetween.

Compression collar 21 supplies an interference fit of 0.015 inches around the entire circumference of cylindrical wall portion 12 and thus exerts an even sealing pressure on the S-slit 16 at all times. Compression collar 21 exerts this constant pressure or pre-load on leaves 17 and 18 to prevent diaphragm portion 11 from stretching or losing its resiliency when the valve is repeatedly opened or closed. Once assembled as described above, gastrostomy port 100 becomes one unitized piece with a one-way entrance valve seal accessing the central lumen of the tubular/tip member 50. The one-way valve permits only entrance into central lumen 51 and prevents any fluid from refluxing or backing up the tube and out the entrance seal.

Figure 3:
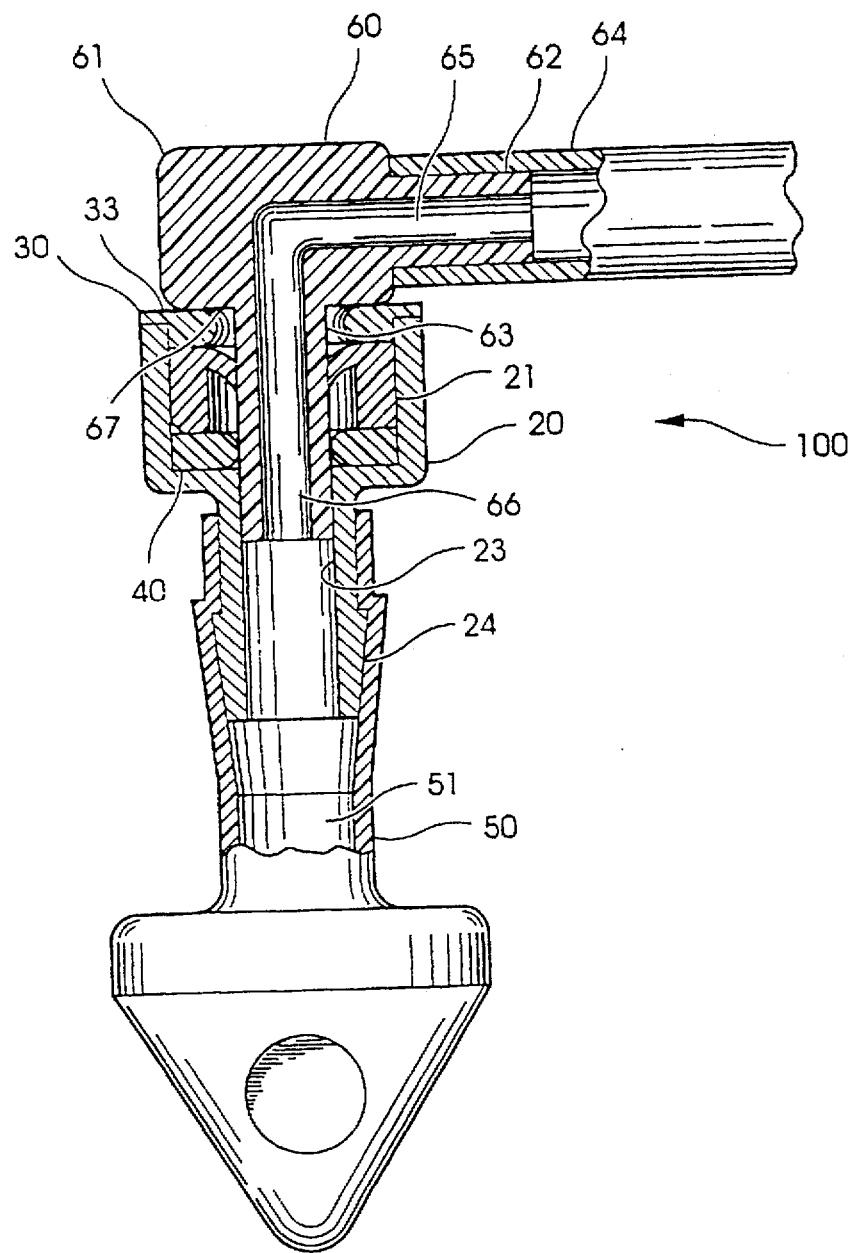
FIG. 3 is a partially cross-sectioned side view of the gastrostomy feeding port of FIGS. 1 and 2, showing a right angle adapter opening the one-way entrance seal and seated within the valve module to provide access into the catheter lumen of the feeding port.

FIG. 3 shows right angle adapter 60 opening entrance "S" slit 16 of valve member 10. Adapter 60 has a rigid injection molded right angle body portion 61, with rear stem 62 and front stem 63. Connected onto rear stem 62 is flexible PVC connecting tube 64. Rear stem 62 has lumen 65 and front stem 63 has lumen 66. When front stem 63 opens entrance seal 10, it seats into annular seating portion 23 of housing member 20. The underside surface 67 on right angle body portion 60 seats firmly on top surface 33 of retainer cap 20. So positioned, lumen 66 of front stem 63 accesses central lumen 51 of tubular/tip member 50. Right angle adapter 60 thus accesses lumen 51 of tubular/tip member 50 to deliver enteral formula or the administration of liquid medication into the body of a patient.

Adapter 60, via connecting tube 64, can be attached to any medication or enteral delivery set whether administered by gravity or a pump delivery method. In addition, adapter 60 can act as a decompression tube to vent gastrostomy port 100 and relieve pressure build up which tends to occur when a gastrostomy feeding port is left in place over a long period of time. When not in use, adapter 60 is removed and valve member 10 closes instantaneously to prevent reflux. Sealing is instantaneous due to compression collar 21 which acts to positively return leaves 17 and 18 to their normally closed position. Adapter 60 can be repeatedly inserted as needed over many months of use without the valve leaking or stretching out of shape.

As described above, a right angle adapter can be inserted into the valve S-slit 16 as needed. The valve remains in its normally closed positively sealed position due to compressive collar 21 acting to bias valve member 10 closed and keeping it closed to prevent reflux of stomach contents out through valve member 10. As such, feeding port 100 requires no internal anti-reflux valve, which might become clogged or stuck. It also does not need any removable valve cap or any stoppers or back up closure caps to add bulk to the outside profile. All functions can take place directly through the entrance seal, thus eliminating the need for anti-reflux valves, valve caps, stoppers, closure caps, or complicated decompression tubes.

Figure 4A:
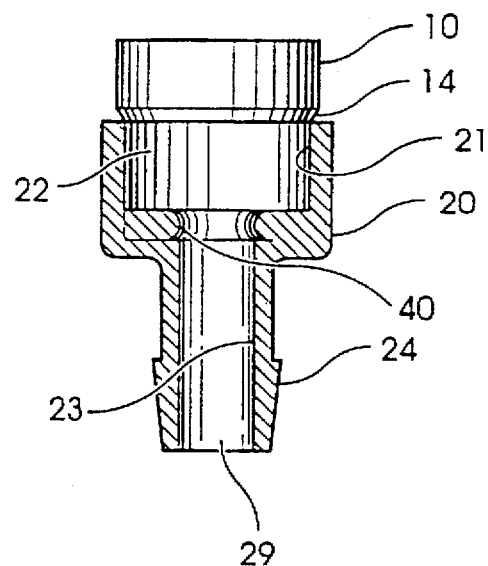
FIG. 4a is a side cross-sectioned view of the valve housing of FIGS. 1–3, showing resilient valve member 10 prior to positioning within cavity 22.
Figure 4B:
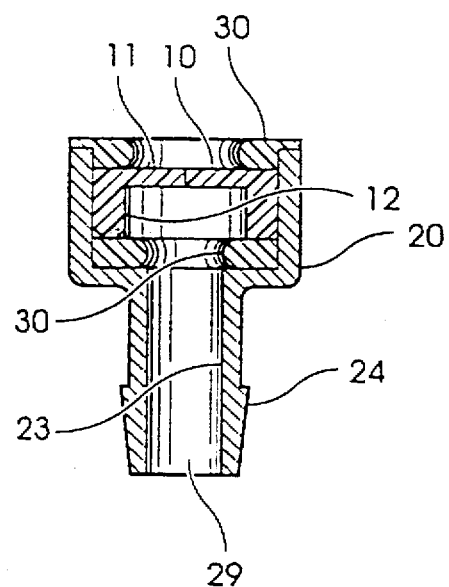
FIG. 4b is a side cross-sectioned view of valve housing 20 of FIG. 4a, showing resilient valve member press fitted into cavity 22, with retainer cap 30 mounted thereon to maintain valve member 10 within cavity 22.

FIG. 4a shows resilient valve member 10 prior to positioning within cavity 22. In FIG. 4a, valve member 10 is uncompressed and is larger in dimension than cavity 22. FIG. 4a further shows how chamfered edge 14 allows for the introduction of cylindrical wall portion 12 into cavity 22 such that valve member 10 can then be press fit into cavity 22 without buckling or distorting diaphragm portion 11. FIG. 4b, showing resilient valve member 10, after it has been press fitted into cavity 22, with retainer cap 30 mounted thereon to maintain valve member 10 within cavity 22.

Figure 5:
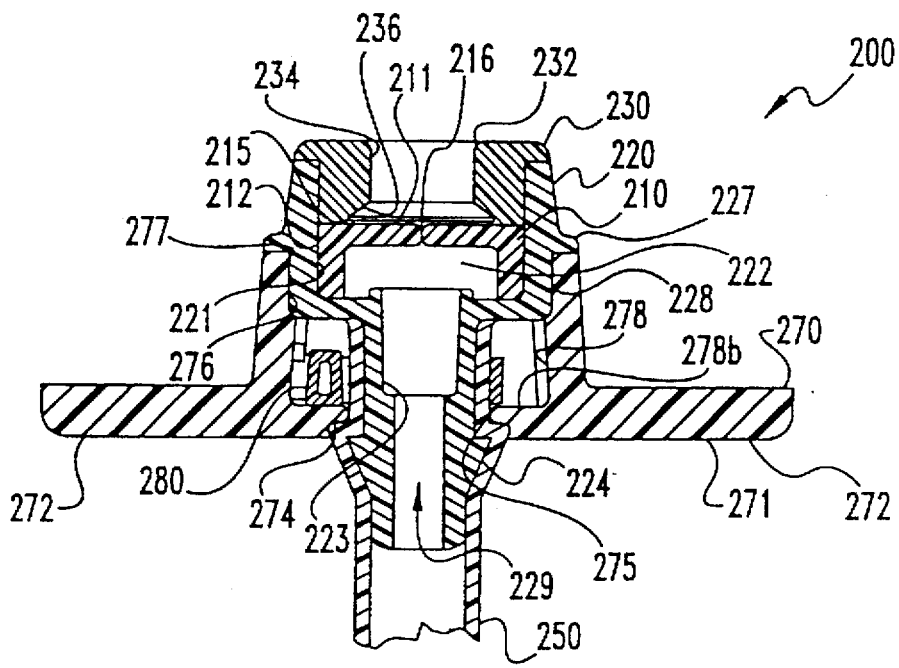
FIG. 5 is a side, cross-sectioned view of a second embodiment of the present invention which usefully converts an implanted PEG feeding tube into a low profile device, and which also directly connects to an enteral feeding adapter without the need for intermediate extension tubing.
Figure 6:
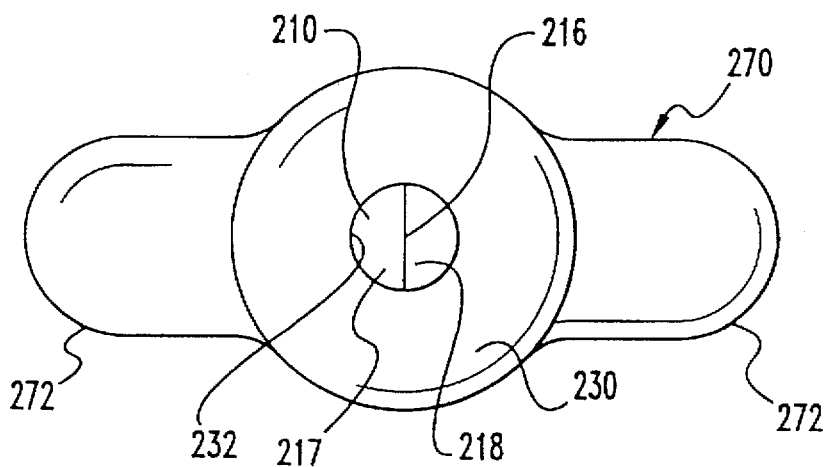
FIG. 6 is a top plan view of the gastrostomy port shown in FIG. 5.
Figure 7:
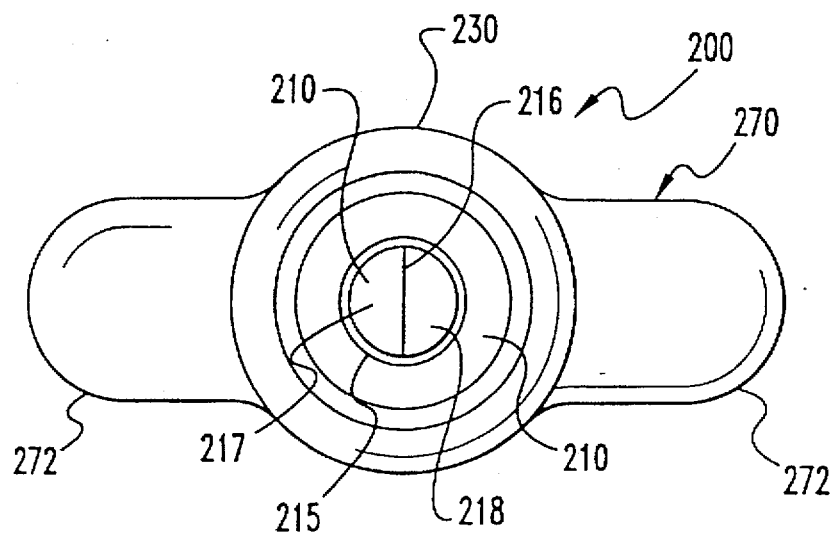
FIG. 7 is a top plan view of the gastrostomy port shown in FIG. 5 with the cap removed.

A second embodiment of the present invention is illustrated in FIGS. 5, 6 and 7 by which a long smooth walled PEG tube that has been previously implanted into a patient can be directly converted to a low profile gastrostomy port. By this conversion, the need to remove the PEG tube and install a separate low profile port is eliminated, thus making the procedure a simpler one for the physician while also reducing the added risk of infection and trauma attendent with complete replacement. Low profile conversion gastrostomy port 200 is also configured to directly connect to an enteral feeding adapter without the need for extension tubing.

Referring to FIG. 5, gastrostomy feeding port 200 is shown which includes resilient valve member 210, valve housing 220, retainer cap 230, and bolster 270, which are collectively connected to PEG tube 250. PEG tube 250 is a common smooth walled PEG tube which has been cut to a suitable length as part of the conversion process. Resilient valve member 210 is made of silicone rubber and has been constructed as a molded one-piece component and is preferably made from shore A 50 to 60 durometer high tear strength medical grade silicone. Resilient valve member 210 includes a diaphragm portion 211 which has a centrally located slit 216 therein. Valve member 210 further has an outer cylindrical wall portion 212 which extends downwardly from the peripheral edge of diaphragm portion 211. Also, valve member 210 includes a contact ring 215 about diaphragm portion 211. Contact ring 215 is more fully depicted in the top plan view of FIG. 7 which has cap 230 removed.

Referring again to FIG. 5, valve housing 220 defines an inner passageway 229 therethrough and includes rigid compression collar portion 221 which defines receiving cavity 222, annular seating portion 223 for seating of an adapter, and annular barb 224. Valve housing 220 also includes a base portion 228 with annular flange 227. Valve housing 220 should be made from a rigid biocompatible material, such as rigid PVC.

Retainer cap 230 defines a top opening 232 intersecting a passage 234 which, in turn, intersects cap cavity 236. Preferably, opening 232, passage 234, and cap cavity 236 are annular. Retainer cap 230 is preferably made of a shore A 70 to 75 durometer semi-rigid PVC, but could be made from another suitable biocompatible material as well. FIG. 6 provides a top plan view of cap 230 assembled on gastrostomy port 200.

Referring again to FIG. 5, gastrostomy feeding port 200 also includes bolster 270 with lower surface 271 and opposing tabs 272. Bolster 270 has an annular wall 276 which forms a chamber 278 opposing surface 271. Chamber 278 has upper opening 277 and is configured to receive valve housing 220. Annular wall 276 adjacent upper opening 277 forms a seal with the valve housing base 228 and abuts annular flange 227. Bolster 270 defines a lower opening 274 intersecting chamber 278 opposite upper opening 277. Lower opening 274 is configured to receive the severed end of PEG tube 250. Sealing ring 275 surrounds opening 274 and reinforces it to make it suitable for press-fit sealing. Bolster 270 is configured so that sealing ring 275 stretches over annular barb 224 with PEG tube 250 thereon and rebounds to clamp PEG tube 250 between sealing ring 275 and annular seating portion 223. Bolster 270 is thus configured so that sealing ring 275 clamps above annular barb 224 when annular wall 276 abuts annular flange 227. Furthermore, when so configured, annular wall 276 seals against housing base 228. The expansive area of surface 271 helps prevent inward migration of the gastrostomy port 200 into the body of a patient. The seal at opening 274 via sealing ring 275 further acts to sealingly prevent foreign materials and fluids from migrating along the outer surface of the PEG tube 250 and into gastrostomy port 200.

Figure 8:
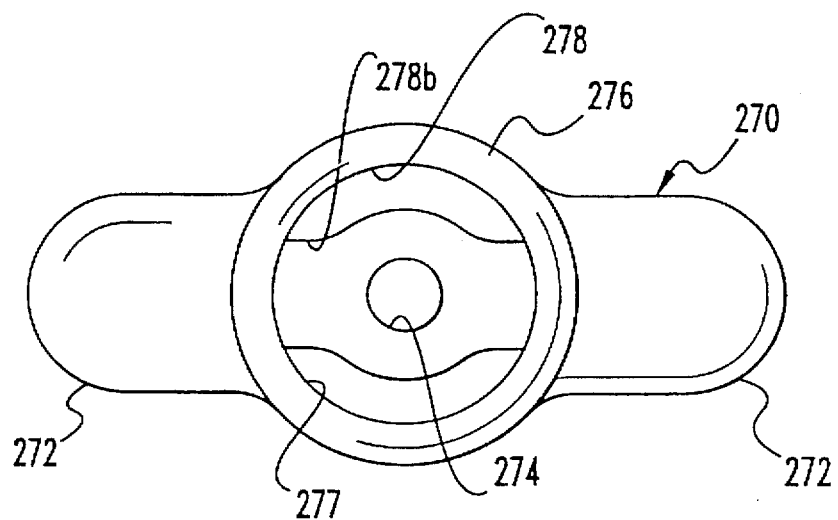
FIG. 8 is a top plan view of the bolster included in the embodiment shown in FIG. 5.

Referring to FIG. 8 as well as FIG. 5, chamber 278 includes a lower chamber portion 278b. Lower chamber portion 278b contains pull tie 280. Pull tie 280 is of a type known to those of skill in the art having an elongate band portion to encircle an object and an engagement mechanism to secure pull tie 280 to the object. Pull tie 280 encircles PEG tube 250 above annular barb 224 to secure it against annular seating portion 223. Preferably, bolster 270 is made of the same silicone material as the valve member 210 and cap 230.

To assemble the valve structure for gastrostomy port 200, valve member 210 is "press" fit into valve housing 220 similar to the method described for gastrostomy port 100 (see FIGS. 4a and 4b and accompanying text herein), with ring 215 of valve member 210 facing upward as shown in FIG. 7. Also, slit 216, which is generally straight configuration, is biased towards a positively sealing closed position by the inwardly directed compressive force from collar 221 which actively biases slit 216 to positively seal valve member 210. Compression collar 221 exerts this constant pressure or pre-load on slit 216 to prevent diaphragm portion 211 from stretching or losing its resiliency when the valve is repeatedly opened or closed.

After valve member 210 has been seated into cavity 222, retainer cap 230 is placed on the top portion of valve housing 220 and affixed thereto by solvent cementing or such other biocompatible bonding method appropriate for joining retainer cap 230 and valve housing 220. Cap wall 236 engages contact ring 215 of valve member 210 to seal guard against leakage under cap 230. Once in place, retainer cap 230 does not exert any axial compressive force upon valve member 210, which could cause distortion of the sealing arrangement. Contact ring 215 provides reinforcement about diaphragm portion 211 and so assists in preventing distortion of the sealing arrangement.

To accomplish the conversion of PEG tube 250 to a low profile feeding port, PEG tube 250 is first clamped and then severed at an appropriate length near the stoma opening. Preferably the length of the cut tube should allow for some free-play between bolster surface 271 and the portion of the PEG tube 250 entering into the stoma site. A preferred range is 1 to 5 centimeters with a more preferred range of 1.5 to 3 centimeters and a most preferred value of about 2 centimeters.

Bolster 270 is then placed on PEG tube 250 working PEG tube 250 through opening 274 until the end of the PEG tube 250 extends beyond opening 277. Annular seating portion 223 is then inserted into PEG tube 250 until the end of PEG tube 250 goes past the annular barb 224 and rests adjacent housing base 228. Pull tie 280 is placed about PEG tube 250 between housing base 228 and annular barb 224 and is pulled to clamp PEG tube 250 between it and annular seating portion 223 of valve housing 220. Pull tie 280 includes a mark placed along a given length of the elongate band portion for alignment with the engagement mechanism. This mark is positioned to correspond to the proper length of pull tie 280 to assure that adequate tension is exerted to the PEG tube 250 for a reliable seal. Consequently, by aligning this mark appropriately, the proper amount of clamping force results and a reliable seal of PEG tube 250 to annular seating portion 223 is consistently obtained. Any extraneous portion of pull tie 280 is then removed by cutting and trimming the excess as close to the engagement mechanism as possible.

Next bolster 270 is moved along PEG tube 250 until annular wall 276 abuts annular flange 227, receiving housing base 228, and sealing ring 275 is above annular barb 224. Tabs 272 provide a convenient point to manipulate bolster 270. As a result, pull tie 280 is enclosed within lower chamber portion 278b so that bolster 270 protects the patient from unpleasant contact therewith and at the same time provides a relatively large surface area to abut the patient's skin and shelter the passage in the patient's body which contains PEG tube 250.

As assembled as described above, gastrostomy port 200 provides a low profile gastrostomy port with a one-way entrance valve seal accessing the central lumen of the PEG tube 250. Gastrostomy port 200 is especially useful for directly converting a PEG tube to a low profile gastrostomy port device. Gastrostomy port 200 provides a secure and reliable connection to PEG tube 250. Furthermore, the one-way valve only permits entry and prevents fluid from refluxing or backing up the tube and out the entrance seal. Also, gastrostomy port 200 can be directly connected to a standard enteral feeding adapter as shown in FIG. 11, thus eliminating the need to use intermediate extension tubing.

Figure 9:
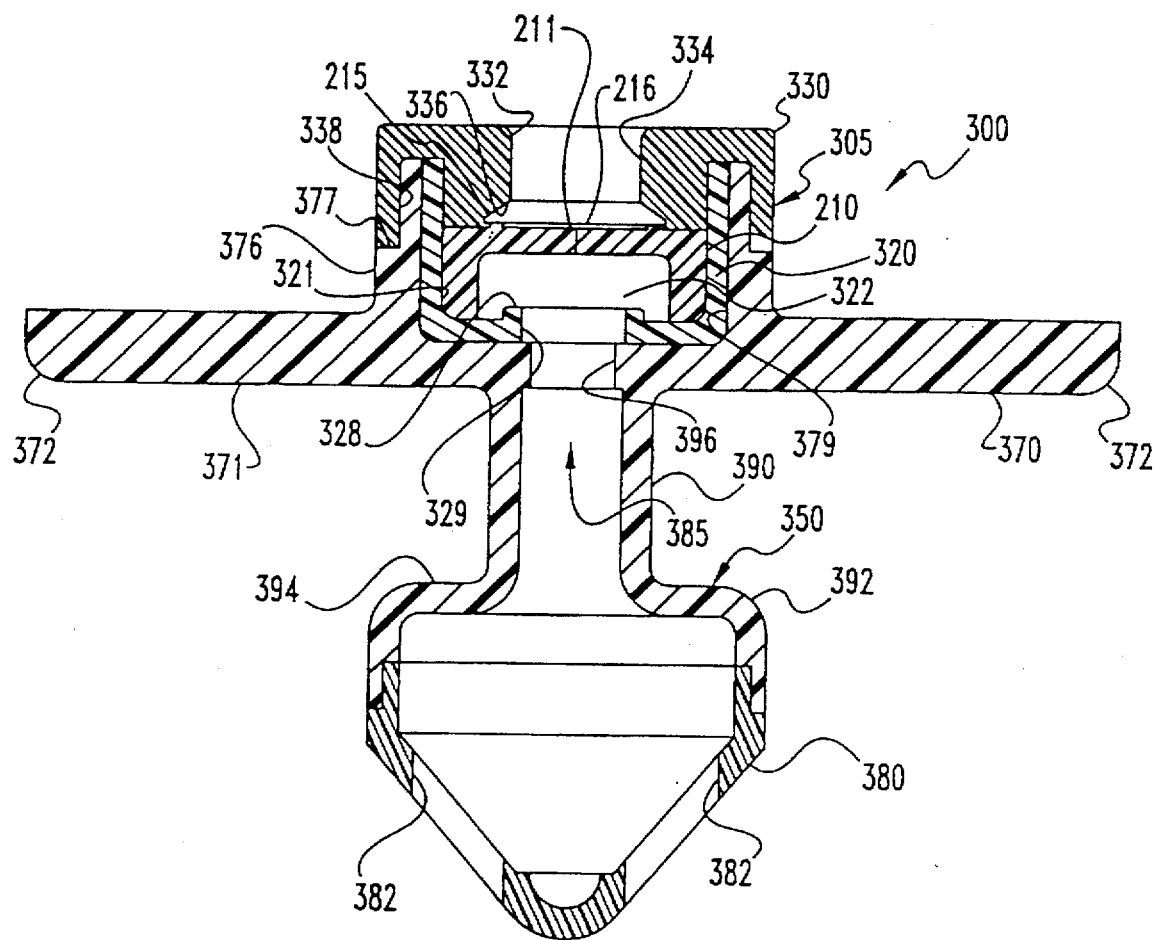
FIG. 9 is a side, cross-sectioned view of a third embodiment of a unitary, fixed length, low profile gastrostomy port of the present invention which directly connects to an enteral feeding adapter without the need for intermediate extension tubing.
Figure 10:
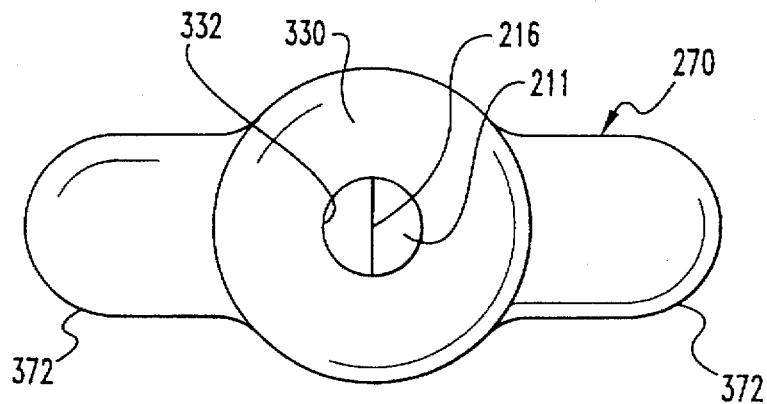
FIG. 10 is a top plan view of the gastrostomy port shown in FIG. 9.
Figure 11:
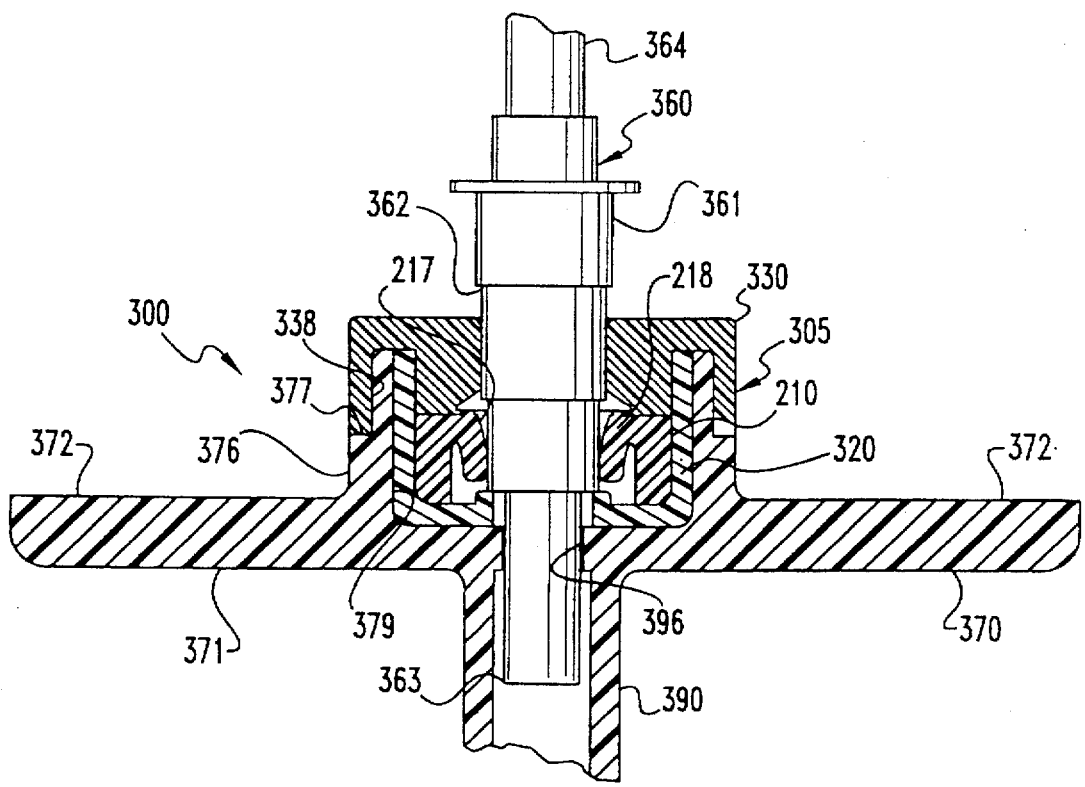
FIG. 11 is a partially cross-sectioned side view of an enteral feeding adapter directly connected to the gastrostomy feeding port of FIGS. 9 and 10.

Another embodiment of the present invention will now be described which provides a unitary fixed length low profile gastrostomy port, as illustrated in FIGS. 9, 10, and 11. Specifically, gastrostomy feeding port 300 is depicted which includes resilient valve member 310, valve housing 320, retainer cap 330, and main port body member 350. Resilient valve member 210 is the same valve member depicted in FIGS. 5–7.

Valve housing 320 defines a lower opening 329 therethrough and includes rigid compression collar portion 321 which defines receiving cavity 322. Valve housing 320 also includes a support base portion 328 adjacent opening 329. Valve housing 320 is injection molded from a rigid plastic such as lexan or polypropylene, but could be a machined part of stainless steel, or made of other suitable biocompatible material as well.

Retainer cap 330, which is made of silicone or other suitable biocompatible material, defines a top opening 332 intersecting passage 334 which, in turn, intersects cap cavity 336. Preferably, opening 332, passage 334, and cap cavity 336 are annular. Retainer cap 330 also defines an annular channel 338 configured to engage main port body member 350 and valve housing 320. Retainer cap 330 is preferably made of the same material as valve member 210.

Gastrostomy feeding port 300 also includes a unitary main port body member 350, silicone body member 350 is made of silicone or other suitable biocompatible material and has a conical tip portion 380 connected to tubular stem portion 390 by a biocompatible adhesive solvent or cement such as RTV. Tubular stem portion 390 has a bell shaped portion 392 with a surface 394 configured for contact against the wall of the patient's stomach. Preferably the length of stem portion 390 allows for some free-play of main port body member 350 implanted in the patient's stomach. A preferred range is 1 to 5 centimeters with a more preferred range of 1.5 to 3 centimeters and a most preferred value of about 2 centimeters. The conical tip 380 defines holes 382. Main port body member 350 defines a passage 385 intersecting the holes 382 and a tube opening 396 in coupling portion 370.

Tubular stem portion 390 is integrally connected to a coupling portion 370 with opposing flaps 372 which aid in the placement and manipulation of gastrostomy feeding port 300. Coupling portion 370 has a lower surface 371 which is configured to contact the patient's skin adjacent the passage in the patient's body containing the tubular stem portion 390. Coupling portion 370 also includes an upper annular wall 376 with an annular shelf 377. Annular wall 376 defines a space 379 for receiving valve housing 320 and is configured to engage annular channel 338 along side compression collar 321. The space 379 is further configured so that opening 329 aligns with tube opening 396 when the valve housing 320 is received therein.

To assemble the valve structure for gastrostomy port 300, valve member 210 is "press" fit into valve housing 320 similar to the method described for gastrostomy ports 100 and 200. Compression collar 321 exerts a constant pressure or pre-load on slit 216 to prevent diaphragm portion 211 from stretching or losing its resiliency after repeated use.

After valve member 210 has been seated into cavity 322, valve housing 320 is placed into space 379 of member 350. The conical tip 380 may be bonded to tubular stem portion 390 either before or after these steps. Next, retainer cap 330 is situated so that compression collar 321 and annular wall 376 engage annular channel 338 and retainer cap 330 abutts annular shelf 377. Once in position, retainer cap 330 is attached to member 350 by a biocompatible adhesive, such as an RTV. When so positioned, retainer cap 330 does not exert any axial compressive force upon valve member 310 which could cause distortion of the sealing arrangement. Together, retainer cap 330 and coupling portion 370 comprise a port head 305 which contains valve housing 320 and resilient valve member 210.

Gastrostomy port 300, as above described and shown in FIGS. 9, 10, and 11, provides a unitary fixed length low profile gastrostomy port with a one-way positively sealing entrance valve. The one-way valve permits only entrance into passage 385 and prevents any fluid from refluxing or backing up the tube and out the entrance seal. Gastrostomy port 300 can be used directly connected to a standard enteral feeding adapter as shown in FIG. 11.

FIG. 11 shows an adapter 360 opening entrance slit 216 of valve member 210 situated in gastrostomy port 300. Adapter 360 has a rigid injection molded body portion 361, with a passage through a base stem portion 362 and front stem portion 363. Connected onto base stem portion 362 is flexible PVC connecting tube 364.

Adapter 360 directly connects to the gastrostomy port 300. The front stem portion 363 passes through top opening 332 and opens valve member 210. Next, front stem portion 363 passes through opening 329, engages tube opening 396, and extends into passage 385. Tube opening 396 is configured so that it seals against front stem portion 363 positioned therein. Just as front stem portion 363 engages tube opening 396, the base stem portion seats against support base 328 of valve housing 320. Not only does support base 328 offer support to the adapter, but also prevents inserting the adapter too far into the gastrostomy port 300. In this supported position, the top opening 332 seals against the base stem portion 362 of adapter 360. Adapter 360 thus accesses passage 385 of member 350 to directly deliver enteral formula or the administration of liquid medication into the body of a patient having a lower seal at tube opening 396 and an upper seal at top opening 332. Between these two seals a support base is provided which limits the extent of penetration of adapter 360 into the gastrostomy port 300 and the valve member 210 opens to allow adapter 360 to pass therethrough. When adapter 360 is removed, valve member 210 closes instantaneously to prevent reflux. Sealing is instantaneous due to compression collar 321 which acts to positively return leaves 217 and 218 to their normally closed position. Adapter 360 can be repeatedly inserted as needed over many months of use without the valve leaking or stretching out of shape.

As can be appreciated, a number of variations of the gastrostomy ports 100, 200 and 300 can be made which fall within the underlying spirit of the invention. For instance, variations in form of the entrance seal can be made from that specifically described herein without departing from the spirit or scope of the underlying invention. Also, varying configurations as to the shape of the valve and corresponding valve receiving cavity, or in the slit within the valve may still fall within the spirit and scope of this invention. With the foregoing in mind, it is apparent to those skilled in the art to make modifications or different configurations of the invention without varying from the invention and the invention is not to be limited to the particular forms herein shown and described except insofar as indicated by the scope of the appended claims.

Accordingly while the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A gastrostomy feeding port for direct sealing connection to an enteral feeding tube adapter having a front stem portion and a base stem portion, comprising:
    a port head defining a top opening configured to allow the front stem portion of the enteral feeding tube adapter to pass therethrough, said top opening being configured to seal about the base stem portion of the adapter;
    a tube opening configured to seal about the front stem portion of the adapter passing through said top opening;
    a one-way entrance valve secured within said port head between said top opening and said tube opening and aligned therewith, said valve opening to permit the adapter to pass therethrough, and said valve closing when the adapter is removed.

2. The gastrostomy feeding port of claim 1, further comprising a support base connected to said port head, said support base being configured to support the adapter within said port head and to limit the amount of penetration by the adapter.

3. A gastrostomy feeding port for connection to an enteral feeding tube adapter having a from stem portion and a base stem portion, comprising:
    a port head defining a first opening opposing a second opening, said first and second openings being configured to allow the front stem portion of the adapter to pass therethrough;
    a one-way entrance valve secured within said port head between said first and second openings and aligned therewith, said valve opening to permit the adapter to pass therethrough, and said valve closing when the adapter is removed to prevent fluid transfer through said port head; and
    wherein said first opening provides a first seal about the base stem portion of the adapter and said second opening provides a second seal about the front stem portion of the adapter when the adapter is inserted into said port head to thereby resist fluid leakage from said port head during repeated and long-term engagement by the adapter.

4. The gastrostomy feeding port according to claim 3, wherein said port head includes a resilient retaining cap defining said first opening and providing said first seal.

5. The gastrostomy feeding port according to claim 3, wherein said port head further includes a resilient o-ring defining said second opening and providing said second seal.

6. The gastrostomy feeding port according to claim 3, wherein said first opening is generally circular with a first diameter, said second opening is generally circular with a second diameter, and said first diameter is larger than said second diameter.

7. The gastrostomy feeding port according to claim 3, further comprising a tube portion in fluid communication with said second opening.

8. The gastrostomy feeding port according to claim 3, further comprising a tube in fluid communication with said second opening and a fastener securing said tube to said port head.

9. The gastrostomy feeding port according to claim 3, wherein said port head has a support base to support the adapter within said port head and to limit the amount of penetration by the adapter.

10. The gastrostomy feeding port according to claim 3, wherein said port head includes a rigid compression collar which defines a valve member receiving cavity and said valve includes a resilient valve member with a diaphragm portion defining a slit therethrough, and said valve member is compressively fit within said cavity to bias said slit to a normally closed position.

11. A kit for converting an percutaneous gastrostomy feeding tube to a low profile gastrostomy feeding port, the tube having a distal end implanted in a patient's body and a proximal end located outside the patient's body, the port being configured to receive a removable enteral feeding port adapter, comprising:
    a port head having a top portion defining a top opening and a base portion defining a lower opening, said port head being configured to allow the adapter to pass therethrough and provide a first seal about the adapter to prevent leakage when the adapter is inserted therethrough;
    a one-way entrance valve secured within said port head between said top and lower openings and aligned therewith, said valve opening to permit the adapter to pass therethrough, and said valve closing when the adapter is removed to prevent transfer of material therethrough;
    a fastener configured to fasten the proximal end of the tube to said base portion of said port head to permit transfer of fluid into the tube from the adapter when the adapter is inserted into said port head.

12. The kit according to claim 11, wherein said base portion includes a stem with an annular barb configured to engage the tube.

13. The kit according to claim 11, wherein said base portion includes a stem with an annular barb configured to engage the tube and said fastener includes a pull tie configured to clamp the tube to said stem.

14. The kit according to claim 13, further comprising a bolster defining an aperture, said bolster being configured to slide over the tube before fastening the tube to said port head and slide over said base portion after fastening the tube to said port head, said bolster defining a chamber configured to house said pull tie when clamped to the tube.

15. The kit according to claim 14, wherein said bolster includes a resilient sealing ring formed about said aperture, said sealing ring is configured to stretch over said annular barb after said pull tie clamps the tube to said stem and is further configured to clamp the tube to said stem after stretching over said annular barb.

16. The kit according to claim 11, wherein said port head includes a rigid compression collar which defines a valve member receiving cavity and said valve includes a resilient valve member with a diaphragm portion defining a slit therethrough, and said valve member is compressively fit within said cavity to bias said slit to a normally closed position.

17. The kit according to claim 11, wherein said fastener includes a pull tie.

18. A gastrostomy feeding assembly for repeated long term use, comprising:

an enteral feeding tube adapter, said adapter having a front stem portion with a first diameter and a base stem portion with a second diameter larger than said first diameter;

a port head defining a first opening opposing a second opening, said first opening receiving said front and base stem portions therethrough and said second opening receiving said front stem portion therethrough;

a one-way entrance valve secured within said port head between said first and second openings and aligned therewith, said valve opening to permit the adapter to pass therethrough, and said valve closing when the adapter is removed to prevent fluid transfer through said port head; and wherein said port head has a support base positioned between said valve and said second opening to engage said base stem portion and prevent passage of said base stem portion through said second opening.

19. The gastrostomy feeding assembly according to claim 18, wherein said support base includes an annular seating portion configured for engagement by said base stem portion.

20. The gastrostomy feeding assembly according to claim 18, wherein said first opening provides a first resilient seal about said base stem portion and said second opening provides a second resilient seal about said front stem portion.

21. The gastrostomy feeding assembly according to claim 20, wherein said support base and said adapter are formed from a polymeric resin compound and have greater rigidity than said said first seal and said second seal.

22. The gastrostomy feeding assembly according to claim 18, wherein said port head includes a rigid compression collar which defines a valve member receiving cavity and said valve includes a resilient valve member with a diaphragm portion defining a slit therethrough, and said valve member is compressively fit within said cavity to bias said slit to a normally closed position.

23. The gastrostomy feeding assembly according to claim 18, further comprising a tube in fluid communication with said second opening and a fastener securing said tube to said port head.

24. A method of converting an percutaneous gastrostomy tube implanted in a patient's body to a low profile gastrostomy feeding port, the tube having a inner portion positioned within the patient's body and a outer portion positioned outside the patient's body to define a fluid passageway therebetween, and the port being configured to receive a removable enteral feeding port adapter, the method comprising:

severing the outer portion of the tube to provide a shorter length of the tube outside the patient's body;

providing a port head defining a top opening opposing a bottom opening and including a valve positioned between the top and bottom openings, the valve being configured to open when the adapter is inserted into the port head and close when the adapter is removed from the port head; and coupling the port head to the outer portion of the tube with a fastener to establish fluid communication between the bottom opening of the port head and the passageway to selectively provide fluid through the tube when the adapter is inserted into the port head.

25. The method of claim 24, wherein the length of the tube outside the patient's body after said severing is in a range of about 1 to 5 centimeters.

26. The method of claim 24, further comprising clamping the outer portion of the tube and measuring the outer portion of the tube before said severing.

27. The method of claim 24, wherein the port head includes a stem with an annular barb defining the bottom opening and said coupling includes inserting the stem into the passageway of the tube through an opening defined by the outer portion.

28. The method of claim 24, further comprising providing a bolster defining an aperture and inserting the tube through the aperture.

29. The method of claim 24, further comprising clamping the outer portion of the tube before said severing, measuring the outer portion of the tube to provide a length of the tube outside the patient's body in a range of about 1 to 5 centimeters after said severing, providing a bolster defining an aperture, and passing the tube through the aperture; and wherein the port head includes a stem with an annular barb defining the bottom opening and said coupling includes inserting the stem into the passageway of the tube after said passing and securing a pull tie about the tube and the stem, the pull tie being located between the valve and the barb, and the aperture of the bolster being located between the pull tie and the barb.

* * * * *